United States Patent [19]

Beutler

[11] Patent Number: 5,506,214

[45] Date of Patent: Apr. 9, 1996

[54] USE OF SUBSTITUTED ADENINE DERIVATIVES FOR TREATING MULTIPLE SCLEROSIS

[75] Inventor: Ernest Beutler, La Jolla, Calif.

[73] Assignee: The Scripps Research Institute, La Jolla, Calif.

[21] Appl. No.: 256,931

[22] PCT Filed: Feb. 18, 1993

[86] PCT No.: PCT/US93/01467

§ 371 Date: Jul. 27, 1994

§ 102(e) Date: Jul. 27, 1994

[87] PCT Pub. No.: WO93/16706

PCT Pub. Date: Sep. 2, 1993

Related U.S. Application Data

[63] Continuation of Ser. No. 838,546, Feb. 19, 1992, Pat. No. 5,310,732, which is a continuation-in-part of Ser. No. 460,351, Jan. 3, 1990, Pat. No. 5,106,837, which is a continuation-in-part of Ser. No. 323,350, Mar. 14, 1989, abandoned, which is a continuation-in-part of Ser. No. 169,618, Mar. 16, 1988, abandoned, which is a continuation-in-part of Ser. No. 825,215, Feb. 3, 1986, abandoned.

[51] Int. Cl.$^6$ .................................................. A61K 31/70
[52] U.S. Cl. .................................................. 514/46; 514/45
[58] Field of Search .................................................. 514/45, 46

[56] References Cited

U.S. PATENT DOCUMENTS

| | | | |
|---|---|---|---|
| 5,106,837 | 4/1992 | Carson et al. | 514/46 |
| 5,310,732 | 5/1994 | Carson et al. | 514/46 |

OTHER PUBLICATIONS

Carrera et al., J. Clin. Invest., 86, 1480–1488 (1990).
Piro, et al., "2–Chlorodeoxy Adenosine: an Effective New Agent for the Treatment of Chronic Lymphocitic Leukemia", Blood, 72:1069–1073 (1988).
Montgomery, et al., "Synthesis of Potential Anticancer Agents. XX. 2–Fluoropurines", J. Am. Chem. Soc., 82:463–468 (1960).
Stoeckler, et al., "C (2') Substituted Purine Nucleoside Analogs", Biochemical Pharmacology, 31:1723–1728 (1982).
Beutler, E. "Cladribine (2–Chlorodeoxy Adenosine)", The Lancet, 340:952–956 (1992).
Beutler, et al., "Antileukemic and Immunosuppressive Activity of 2–Chloro—2'—Deoxy Adenosine", Proc. Natl. Acad. Sci., 81: 2232–2236 (1984).
Carson, et al., "Deoxycytidine Kinase–Mediated Toxicity of Deoxy Adenosine Analogs Towards Murine L1210 Leukemia in Vivo", Proc. Natl. Acad. Sci., 77:6865–6869 (1980).
Liliemark, et al., "On The Bioavailability of Oral and Sub Cutaneous 2–Chloro–2'—Deoxy Adenosine in Humans: Alternative Routes of Administration," J. of Clinical Oncology, 10: 1514–1518 (1992).
Hershfield et al., "Effects of Mutational Loss of Adenosine Kinase and Deoxycytidine Kinase on Deoxy ATP Accumulation and Deoxy Adenosine Toxicty in Cultured Cem Human T–Lymphoblastoid Cells", J. Of Biol. Chem., 257:6380–6386 (1982).
Chan et al., "Deoxycytidine Excretion by Misuse Peritoneal Macrophages: Its Implication in Modulation of Immunological Functions", J. of Cellular Phys., 111:28–32 (1982).
Juliusson et al., "Subcutaneous Injections of 2–Chloro–2' Deoxy Adenosine (COA) as Treatment . . ." Blood, 80: Suppl. 1, 1427 (1992).
Fredrikson et al., Acta. Neurol Scand., 1987, 75, 352–355.
Huber et al., J. Exp. Med., 1984, 160, 310–316.
Saven et al., J. Clin. Oncology 1993, 671–678 vol. 11.
Kearns et al., Cancer Research 1994, 54, 1235–1239.
Weilbach et al., Nervenarzt, 1995, 66, 299–303.

Primary Examiner—José G. Dees
Assistant Examiner—Barbara S. Frazier
Attorney, Agent, or Firm—Donald G. Lewis

[57] ABSTRACT

Treatment of patients having multiple sclerosis with therapeutic agents containing substituted adenine derivatives such as 2-chloro-2'-deoxyadenosine is shown to markedly ameliorate the disease condition.

6 Claims, No Drawings

USE OF SUBSTITUTED ADENINE DERIVATIVES FOR TREATING MULTIPLE SCLEROSIS

STATEMENT OF GOVERNMENT RIGHTS

This invention was made with government support under FDA grant FD-R-000280 and NIH grant numbers NS30218 and RR00833. The government has certain rights in the invention.

CROSS-REFERENCE TO RELATED APPLICATIONS

This application is a national phase application of copending International Application PCT/US 93/01467 filed Feb. 18, 1993, which is a continuation of copending U.S. application Ser. No. 838,546, now U.S. Pat. No. 5,310,732, filed Feb. 19, 1992, which was a continuation-in-part of copending application Ser. No. 460,351, filed Jan. 3, 1990, now U.S. Pat. No. 5,106,837, that was a continuation-in-part of copending application Ser. No. 323,350 filed Mar. 14, 1989, now abandoned, that was a continuation-in-part of copending application Ser. No. 169,618, filed Mar. 16, 1988, now abandoned, that is a continuation-in-part of copending application Ser. No. 825,215, filed Feb. 3, 1986, now abandoned.

DESCRIPTION

TECHNICAL FIELD

This invention relates to therapeutic methods for treating multiple sclerosis. More particularly, this invention relates to the use of substituted adenine derivatives for treating multiple sclerosis.

BACKGROUND OF THE INVENTION

Multiple sclerosis (MS) is the result of demyelination in the brain and spinal cord (central nervous system). Symptoms resulting from this demyelination include weakness, visual impairment, incoordination, and paresthesia (abnormal tingling). The course of the disease is largely unpredictable, but often progresses through a cycle of exacerbation of symptoms followed by remission.

Conventional treatments presently employ therapy with ACTH or corticosteroids such as prednisone. Controlled studies suggest that such treatments induce more rapid clearing of acute symptoms and signs but leave the long-term outcome of the disease unaffected. Long-term maintenance therapy with ACTH or corticosteroids is contraindicated. Evidence indicates that immunosuppressant agents have no long-term benefit. (*Cecil, Textbook of Medicine*, Beeson et al., eds., 15th ed., W. B. Saunders Company, Philadelphia, (1979) page 847)

The etiology of multiple sclerosis is unknown but is linked to a variety of genetic and environmental factors. Both cell-mediated and humoral immune responses, triggered by extraneous or autoantigens may contribute to the pathogenesis of multiple sclerosis. Certain immune response genes may be associated with an increased susceptibility to the disease. The disease may be mediated by T cells that recognize an as yet unidentified autoantigen. For example, experimental allergic encephalomyelitis (EAE), an animal model of demyelinating diseases such as multiple sclerosis, can be induced by immunizing mice with whole myelin or specific myelin components such as myelin basic protein.

In humans with multiple sclerosis, exacerbations are correlated with high levels of neopterin in blood and cerebrospinal fluid. Neopterin is a factor released from monocytes and macrophages in the presence of activated T-cells, thereby implicating these cells as being involved in multiple sclerosis exacerbations. (Fredrickson et al. (1987), Acta Neurol. Scand., 75:352–355; Huber et al. (1984), J. Exp. Med., 160:310–316). At the microscopic level, monocytes, microglial cells (macrophages of the central nervous system), and activated T-cells are found within the demyelinated regions of the nerve cells during multiple sclerosis exacerbations. (*Cecil, Textbook of Medicine* (1979), Beeson et al. (eds.), W. B. Saunders Co., Philadelphia, Pa.).

Various conventional treatment methodologies have been employed to ameliorate the symptoms of multiple sclerosis. Many of these are directed to use of palliative, anti-inflammatory agents. No treatment to date has had any consistent positive effect on the course of the disease.

Recently, the art has described the use of specific deoxyribosides as anti-inflammatory agents. For instance, U.S. Pat. No. 4,481,197 (Rideout et al.) relates to the use of unsubstituted 3-deaza-2'-deoxyadenosine derivatives in the treatment of inflammation. U.S. Pat. No. 4,381,344 (Rideout et al.) relates to a process for the synthesis of deoxyribosides that utilizes a bacterial phosphorylase.

A deoxyriboside derivative, 2-chloro-2'-deoxyadenosine (CdA), has been found to be an effective agent for the treatment of chronic lymphocytic leukemia and some T cell malignancies. (Carson et al. (1984) Proc. Natl. Acad. Sci. U.S.A., 81:2232–2236; Piro et al. (1988), Blood 72:1069–1073) The pharmacokinetics of orally and subcutaneously administered 2-chloro-2'-deoxyadenosine in the treatment of chronic lymphocytic leukemia have been described and compared. (Liliemark et al. (1992) Journal of Clinical Oncology, 10, (10): 1514–1518; Juliusson et al. (1992) Blood, 80 (Suppl. 1): 1427) Chronic lymphocytic leukemia is a malignancy of B lymphocytes that bear the Leu-1 surface antigen.

The Leu-1 B cells represent a minor proportion of the normal pool of B lymphocytes, usually less than 20 percent. The Leu-1 B cells express surface markers that are typically found on monocytes (Mac-I antigen) and T-lymphocytes (Leu-1 antigen). Approximately 10 percent of patients with chronic lymphocytic leukemia exhibit accompanying autoimmunity, and recently, Leu-1 B cells have been implicated in the pathogenesis of autoimmune diseases.

Phase I clinical trials on human patients with chronic lymphocytic leukemia indicate that infusion of increasing doses of 2-chloro-2'-deoxyadenosine [0.1–0.5 milligrams per kilogram of body weight per day (mg/kg/day)] yielded increasing plasma concentrations of the drug [10–50 nanomolar (nM)]. Those infusions indicated that the drug was well tolerated and did not induce nausea, vomiting or fever. The dose-limiting toxicity was bone marrow suppression, which usually occurred at doses greater than about 0.2 mg/kg/day or at plasma levels of greater than about 20 nM.

Other studies, Montgomery et al. (1959) J. Am. Chem. Soc., 82:463–468, indicated that 2-fluoroadenosine exhibits a relatively high degree of cytotoxicity. Those workers reported that C57 black mice implanted with Adenocarcinoma 755 (Ad755) could tolerate only about 1 milligram per kilogram of body weight. 2-Fluoroadenosine was found to be inactive at that level against Ad755 as well as leukemia L1210 and the Erlich ascites tumor.

U.S. Pat. No. 4,751,221 and its division No. 4,918,179 to Watanabe et al. describe the synthesis and use of several 2-substituted-2'-deoxy-2'-fluoroarabino-furanosyl nucleosides including adenine derivatives. Those compounds were said to have anti-tumor and antitrypanosomal biological activities. Cytotoxicity data showing anti-tumor activity of 2-amino- 6-thiopurine, guanine and thiopurine derivatives against murine and human cell lines were reported.

U.S. Pat. No. 5,034,518 to Montgomery et al. teaches the synthesis of 2-substituted-2'-deoxy-2'-fluoroaraadenosines. Those compounds were said to have anticancer activity, and data for prolongation of life of mice transplanted with P388 leukemia cells were provided.

The biochemical activity of 2-CdA in cells has been reviewed by Ernest Beutler. (The Lancet (1992), 340: 952–956—incorporated herein by reference)

The 2',3'-dideoxynucleosides are phosphorylated at the 5'-position in T cells to form the 5'-nucleotide triphosphate derivatives. Those derivatives are well known to be substrates for reverse transcriptase molecules. (Ono et al. (1986) Biochem. Biophys. Res. Comm., 2:498–507)

Those 2',3'-dideoxynucleoside 5'-triphosphates are also utilized by mammalian DNA polymerases beta and gamma. (Waquar et al. (1984) J. Cell. Physiol., 121:402–408) They are, however, poor substrates for DNA polymerase-alpha, the main enzyme responsible for both repair and replicative DNA synthesis in human lymphocytes. In part, these properties may explain the selective anti-HIV activity of the 2',3'dideoxynucleosides.

Chan et al. (1982) J. Cell Physiol., 111:28–32 studied the pathways of pyrimidine nucleotide metabolism in murine peritoneal macrophages and monocytes, and reported undetectable levels of deoxycytidine kinase or thymidine kinase in these cells. High levels of adenosine kinase were found, however.

Similar high levels of adenosine kinase have been found in human monocytes and human monocyte-derived macrophages (MDM). MDM were found to exhibit about one-tenth to about one-fourth the nucleoside kinase activity of GEM T lymphoblasts (e.g. ATCC CCL 119) toward uridine, deoxycytidine and thymidine, and about two-thirds the adenosine kinase activity of GEM cells. In addition, that adenosine kinase activity of MDM cells was at least about 10-fold higher than any of the other kinase activities. Those studies also indicated relatively low levels of nucleoside phosphorylation using AZT, dideoxycytidine (ddC) and 2',3'-dideoxyadenosine (ddA) in intact GEM T lymphoblasts and still lower levels with the MDM.

Several 2-substituted adenosine derivatives have been reported not to be deaminated by adenosine deaminase. For example, Coddington (1965) Biochim. Biophys. Acta, 99:442–451 reported that deoxyadenosine-1-N-oxide, as well as 2-hydroxy-, 2-methyl-, 2-chloro-, 2-acetamido-, and 2-methylthioadenosines were neither substrates nor inhibitors for adenosine deaminase. Montgomery, in *Nucleosides, Nucleotides, and Their Biological Applications*, Rideout et al. eds., Academic Press, New York, page 19 (1983) provides a table of comparative $K_m$ and $V_{max}$ data for the deamination of adenosine, 2-haloadenosines 2-halo-deoxyadenosines and 2-fluoroarabinoadenosine that also indicates that those 2-halo adenine derivatives are poor substrates for the enzyme relative to adenine itself. Stoeckler et al. (1982) Biochem. Pharm., 31:1723–1728 reported that the 2'-deoxy-2'-azidoribosyl and 2'-deoxy-2'-azidoarabinosyl-adenine derivatives were substrates for human erythrocytic adenosine deaminase, whereas work of others indicated 2-fluoroadenosine to have negligible activity with adenosine deaminase.

2-Chloro-2'-deoxyadenosine is phosphorylated by nondividing (normal) human peripheral blood lymphocytes and is converted to the 5'-triphosphate. This adenine derivative is not catabolized significantly by intact human cells or cell extracts, and is phosphorylated efficiently by T lymphocytes. (Carson et al. (1980) Proc. Natl. Acad. Sci. USA, 77:6865–6869)

As discussed before, high levels of adenosine kinase have been found in murine peritoneal macrophages and in human monocytes. Adenosine kinase can phosphorylate 2'-deoxyadenosine derivatives, but does so less efficiently than deoxycytidine kinase. (Hershfield et al. (1982) J. Biol. Chem., 257:6380– 6386)

Chemotherapeutic agents are described hereinafter that may be employed as therapeutic agents in the treatment of multiple sclerosis.

SUMMARY OF THE INVENTION

The present invention contemplates a method for treating multiple sclerosis. In this method, a patient having multiple sclerosis is treated with a composition having a pharmacologically acceptable carrier and a substituted adenine derivative dissolved or dispersed therein. The substituted adenine derivative is present in the pharmacologically acceptable carrier in an amount sufficient to provide a therapeutically effective dose over the course of treatment.

Preferred substituted adenine derivatives useful for treating multiple sclerosis may be represented by Formula I having a structural formula corresponding to:

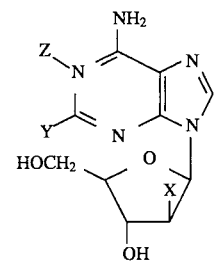

wherein Z is O⁻ or absent,

Y is hydrogen or a substituent containing one to about 20 atoms that is free from net ionic charge at physiological pH values, provides a soluble adenine derivative and whose presence on the adenine moiety inhibits deamination of the adenine derivative by adenosine deaminase; and X is hydrogen or fluoro, with the proviso that Y is hydrogen only when Z is present.

Particularly preferred compounds of Formula I are free of the Z group; i.e, Z is absent, and contain a halo group at the 2-position. The most preferred compounds are 2-chloro-2'-deoxyadenosine and 2-chloro-2'-deoxy-2'-arafluoroadenosine.

Methods for synthesizing all of the above compounds are indicated in U.S. Pat. No. 5,106,837 (Carson et al., Apr. 21, 1992, incorporated herein by reference).

The invention teaches that the disease condition of a patient having multiple sclerosis may be ameliorated by administration of an amount of the above-described composition having a sufficient quantity of the compound of Formula I to provide a therapeutically effective dose. Exemplary dosages range from about 0.04 to about 1.0 mg/kg/day, with dosages of about 0.04 to about 0.2 mg/kg/day being more preferred. Typically, the amount is sufficient to provide a concentration in the patient's plasma of about 0.5 nanomolar (nM) to about 50 nM, more preferably of about 1 nM to about 10 nM.

Preferably, the agent contemplated for use in the present invention is a 2-halo-2'-deoxyadenosine (2-halo-2'-deoxy-9, 1'-beta-ribofuranosyladenine) or a 2-halo-2'-deoxy-2'-arafluoroadenosine, and most preferably the halo group is chloro.

A further aspect contemplated by the present invention comprises the use of subcutaneous injection for administering an effective amount of the active ingredient (agent) of the invention for treating multiple sclerosis.

An alternative aspect contemplated by the present invention comprises the peroral administration of an effective amount of the active ingredient (agent) of the invention in a method of treating disease. Preferred compounds of Formula I for oral administration include compounds in which X is fluoro.

In each of the before-described methods, the substituted 2'-deoxyadenosine derivative is administered in a therapeutically effective amount. The effect of a compound of Formula I is dependent upon the route of administration and upon the time and dosage. As a consequence, one can tailor the dosage and duration for which a particular compound is administered to the stage of the disease and the condition of the patient being treated. Where the stage of multiple sclerosis is advanced or life-threatening, treatment may be more aggressive, and a therapeutically effective amount is an amount that is sufficient to kill at least 50 percent of the monocytes present but is less than that which substantially impairs bone marrow function as determined by usual procedures when administration is in vivo. The monocyte killing amount of a compound of Formula I is another measure of a therapeutically effective dose and monocyte death is measured at a time seven days after the initial administration.

DETAILED DESCRIPTION OF THE INVENTION

A. Compounds

The present invention contemplates the use of substituted adenine derivatives, i.e. substituted- 2'-deoxy-arabinofuranosyladenine, for treating multiple sclerosis. Preferred substituted adenine derivatives have a structure represented by the following formula, viz. Formula I:

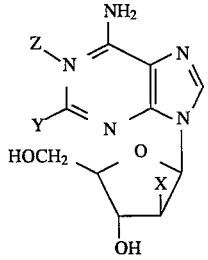

wherein Z is an oxide radical (O⁻) or is absent;

Y is hydrogen or a radical containing one to about twenty atoms that is free from net ionic charge at physiological pH values, provides a soluble adenine derivative, and whose presence on the adenine moiety inhibits deamination of the adenine derivative by adenosine deaminase; and X is hydrogen or fluorine, with the proviso that Y is hydrogen only when Z is present.

Preferably, Y is chloro. Other Y substituents may be selected from the group consisting of lower alkyl, lower alkanoylamido, lower alkylthio and hydroxyl radicals. In particularly preferred embodiments, when Y is chloro, X is fluorine.

The preferred compound included in Formula I is 2-chloro-9,1,'-beta-D-2'-deoxyribosyladenine, otherwise known as 2-chlorodeoxyadenosine or CdA.

Of the compounds of Formula I, those where X is fluoro are among the preferred compounds for use by oral administration.

Other illustrative compounds included in Formula I are:
2-bromo-9,1'-beta-D-2'-deoxyribosyladenine;
2-methyl-9,1'-beta-D-2'-deoxyribosyladenine;
2-fluoro-9,1'-beta-D-2'-deoxyribosyladenine;
2-acetoamido-9,1'-beta-D-2'-deoxyribosyladenine;
2-methylthio-9,1'-beta-D-2'-deoxyribosyladenine; ....
2-chloro-9,1'beta-2'-deoxy-2'-fluoro-D-arabinofuranosyladenine;
2-bromo-9,1'-beta-2'-deoxy-2'-fluoro-D-arabinofuranosyladenine;
2-(N-acetamido)-9,1'-beta-2'-deoxy-2'-fluoro-D-arabinofuranosyladenine;
2-methylthio-9,1'-beta-2'-deoxy-2'-fluoro-D-arabinofuranosyladenine.

Further illustrative of compounds of Formula I include the following arabinofuranosyl derivatives of adenine:
2-methyl-9,1'-beta-2'-deoxy-2'-fluoro-D-arabinofuranosyladenine;
2-isopropyl-9,1'-beta-2'-deoxy-2'-fluoro-D-arabinofuranosyl-adenine;
2-hydroxy-9,1'-beta-2'-deoxy-2'-fluoro-D-arabinofuranosyladenine;
2-chloro-9,1'-beta-2'-deoxy-2'-fluoro-D-arabinofuranosyladenine-1-N-oxide;
2-fluoro-9,1'-beta-2'-deoxy-2'-fluoro-D-arabinofuranosyladenine-1-N-oxide;
2-bromo-9,1'-beta-2'-deoxy-2'-fluoro-D-arabinofuranosyladenine-1-N-oxide;
2-methyl-9,1'-beta-2'-deoxy-2'-fluoro-D-arabinofuranosyladenine-1-N-oxide;
2-(N-acetamido)-9,1'-beta-2'-deoxy-2'-fluoro-D-arabinofuranosyladenine-1-N-oxide;
2-hydroxy-9,1'-beta-2'-deoxy-2'-fluoro-D-arabinofuranosyladenine-1-N-oxide;
2-(2-methylbutyl)-9,1'-beta-2'-deoxy-2'-fluoro-D-arabinofuranosyladenine-1-N-oxide;
2-fluoro-9,1'-beta-D-2'-deoxyadenosine-1-oxide; and
2-chloro-9,1'-beta-D-2'-deoxyadenosine-1-oxide.

It is noted that when X is hydrogen the sugar ring can be named as a 2'-deoxyribosyl or 2'-deoxyarabinofuranosyl radical. Both nomenclatures are utilized herein. When the class of compounds embraced by Formula I is discussed, all of the compounds are considered herein as derivatives of arabinose. However, when specific compounds of the subclass where X=H are discussed, the more familiar deoxyribose nomenclature is used, such as in deoxyadenosine. These compounds are also referred to herein more simply as adenine derivatives.

In the above formulas, and in all other formulas shown herein, hydrogen atoms on the purine and furanosidyl rings that are not needed to show conformation about a particular bond are not shown. Thus, the 8-position adenine hydrogen is not shown.

It is also to be understood that the D isomers of compounds of the formulas are the isomers contemplated. It is further to be noted that the designation "halo" used herein is meant to include fluorine, chlorine and bromine derivatives, and to exclude iodine derivatives, which are unstable and decompose, and astatine derivatives that are radioactive.

Where specific halogen derivatives are intended, those compounds are named specifically.

As used herein, "a substituent free from net ionic charge" includes both charged and uncharged radicals, wherein when the substituent radical is charged, an internal zwitterionic charge pair is present that results in the absence of a net ionic charge for the molecule at physiologic pH values. N-oxide compounds are exemplary of such substituents.

As used herein, a "soluble adenine derivative" is an adenine derivative which is able to dissolve and remain soluble in a body fluid such as blood at a therapeutically effective dose as is discussed hereinafter.

As used herein, a "substituent whose presence on the adenine moiety inhibits deamination of an adenine derivative by adenosine deaminase" is one that, when 100 microliters of a 1 millimolar solution of the substituted adenine derivative is incubated for three hours at room temperature with 25 units of calf spleen adenosine deaminase (1 unit catalyzes the deamination of 1 micromole of adenosine per minute), produces a single UV-absorbing spot upon cellulose-thin layer chromatography of the reaction mixture whose $R_f$ value is the same as that of the substituted adenine derivative used.

The metabolism of a compound by adenosine deaminase can be investigated by the following procedure. The individual nucleosides, at concentrations from 5–200 μM in 10 mM sodium phosphate, pH 7.5, are incubated at 18–20 degrees C. with 0.01 EU/ml calf intestinal adenosine deaminase. The change in the optical density at 265 nm and 250 nm is monitored spectrophotometrically. The $K_m$ and $V_{max}$ values are determined by the Lineweaver-Burke method utilizing the $\Delta E^M_{265}$ between adenosine and inosine.

The ratio $V_{max}/K_m$ also provides a measure of relative efficiency of deamination by the enzyme. A substituent that provides a $V_{max}/K_m$ ratio that is about 1 percent or less than that for the ratio obtained using 2'-deoxyadenosine is also a "substituent whose presence on the adenine moiety inhibits deamination of an adenine derivative by adenosine deaminase."

As used herein, lower alkyl radicals include $C_1$–$C_6$ straight chain, branched and cyclic alkyl groups, for example, methyl, ethyl, n-butyl, t-butyl, n-hexyl, 1-ethylbutyl, cyclopentyl, cyclohexyl and the like. Lower alkanoylamido radicals include $C_1$–$C_6$ radicals, for example, formamido, acetylamido, propionamido, hexamoylamido and the like. Lower alkylthio radicals include $C_1$–$C_6$ straight chain, branched and cyclic alkyl groups as discussed above linked to a thio radical.

The pharmacologically acceptable salts of a compound of Formula I are also utilized. The phrase "pharmacologically acceptable salts," as used herein, refers to non-toxic acid addition salts that are generally prepared by reacting a compound with a suitable organic or inorganic acid. Representative salts include the hydrochloride, hydrobromide, sulfate, phosphate, citrate, acetate, maleate and the like.

B. Compositions

A compound of Formula I dissolved or dispersed in or together with a pharmacologically acceptable carrier constitutes a composition of this invention.

A compound of Formula I and its pharmacologically acceptable salts are useful in both short and long term treatment. For instance, a 2-substituted-9,1'-beta-2'-deoxy-2'-fluoro-D-arabinofuranosyladenine is administered to the patient internally, e.g., subcutaneously by injection, parenterally, orally, or rectally as a suppository, in an effective amount.

Although a compound of Formula I and its pharmacologically acceptable salts can be administered as the pure chemical, it is preferred that it be administered as a pharmaceutical composition. In either event, it is administered in an amount sufficient to provide a therapeutically effective dose as is discussed hereinafter.

Accordingly, the present invention utilizes a pharmaceutical composition comprising a therapeutically effective dose of a compound of Formula I or a pharmacologically acceptable salt thereof, hereinafter referred to as the "active ingredient" or "agent," dissolved or dispersed in a pharmacologically acceptable carrier or diluent.

A pharmaceutical composition is prepared by any of the methods well known in the art of pharmacy all of which involve bringing into association the active compound and the carrier therefor. For therapeutic use, a compound utilized in the present invention can be administered in the form of conventional pharmaceutical compositions. Such compositions can be formulated so as to be suitable for oral, subcutaneous, or parenteral administration, or as suppositories. In these compositions, the agent is typically dissolved or dispersed in a physiologically tolerable carrier.

A carrier or diluent is a material useful for administering the active compound and must be "pharmacologically acceptable" in the sense of being compatible with the other ingredients of the composition and not deleterious to the recipient thereof. Thus, as used herein, the phrases "physiologically tolerable" and "pharmacologically acceptable" are used interchangeably and refer to molecular entities and compositions that do not produce an allergic or similar untoward reaction, such as gastric upset, dizziness and the like, when administered to a mammal. The physiologically tolerable carrier can take a wide variety of forms depending upon the preparation desired for administration and the intended route of administration.

As an example of a useful composition, a compound of Formula I can be utilized in liquid compositions such as sterile suspensions or solutions, or as isotonic preparations containing suitable preservatives. Particularly well-suited for the present purposes are injectable media constituted by aqueous injectable isotonic and sterile saline or glucose solutions. Additional liquid forms in which these compounds can be incorporated for administration include flavored emulsions with edible oils such as cottonseed oil, sesame oil, coconut oil, peanut oil, and the like, as well as elixirs and similar pharmaceutical vehicles.

The agents can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like in addition to the agent. The preferred lipids are the phospholipids and the phosphatidyl cholines (lecithins), both natural and synthetic.

Methods to form liposomes are known in the art. See, for example, Prescott, Ed., Methods in Cell Biology, Volume XIV, Academic Press, New York, N.Y. (1976), p. 33 et seq.

An agent of Formula I can also be used in compositions such as tablets or pills, preferably containing a unit dose of the compound. To this end, the agent (active ingredient) is mixed with conventional tableting ingredients such as corn starch, lactose, sucrose, sorbitol, talc, stearic acid, magnesium stearate, dicalcium phosphate, gums, or similar materials as non-toxic, physiologically tolerable carriers. The tablets or pills can be laminated or otherwise compounded to provide unit dosage forms affording prolonged or delayed action.

It should be understood that in addition to the aforementioned carrier ingredients the pharmaceutical formulation described herein can include, as appropriate, one or more additional carrier ingredients such as diluents, buffers, flavoring agents, binders, surface active agents, thickeners, lubricants, preservatives (including antioxidants) and the like, and substances included for the purpose of rendering the formulation isotonic with the blood of the intended recipient.

The tablets or pills can also be provided with an enteric layer in the form of an envelope that serves to resist disintegration in the stomach and permits the active ingredient to pass intact into the duodenum or to be delayed in release. A variety of materials can be used for such enteric layers or coatings, including polymeric acids or mixtures of such acids with such materials as shellac, shellac and cetyl alcohol, cellulose acetate phthalate, and the like. A particularly suitable enteric coating comprises a styrene-maleic acid copolymer together with known materials that contribute to the enteric properties of the coating. Methods for producing enteric coated tablets are described in U.S. Pat. No. 4,079,125 to Sipos, which is herein incorporated by reference.

The term "unit dose", as used herein, refers to physically discrete units suitable as unitary dosages for administration to patients, each such unit containing a predetermined quantity of the agent calculated to produce the desired therapeutic effect in association with the pharmaceutically acceptable diluent. Examples of suitable unit dosage forms in accord with this invention are tablets, capsules, pills, powder packets, granules, wafers, cachets, teaspoonfuls, dropperfuls, ampules, vials, segregated multiples of any of the foregoing, and the like.

Administration of the compound by subcutaneous injection is a particularly attractive mode of administration due to the favorable pharmacokinetics of this mode of administration.

Oral administration of the compound is also an attractive mode of administration. One drawback usually associated with oral administrations of bioactive nucleoside compounds, however, is their potential decomposition in the acidic conditions of the stomach. That is, the glycosidic bond tends to hydrolyze under acid conditions.

However, where oral administration is desired, substitutions on the 2-position of the adenine ring of the compound of Formula I are utilized along with a 2'-fluoro-substituted arabinofuranosidyl ring.

Marquez et al. (1987) Biochem. Pharm., 36:2719– 2722 reported preparation of 2'-fluoro-2',3'-dideoxyribose and 2'-fluoro-2',3'-dideoxyarabinose derivatives of adenine. Their findings stated that both derivatives were stable at a pH value of 1 at 37 degrees C., whereas dideoxyadenosine had a half-time of 35 seconds under those conditions.

The ability of an adenine derivative to be or not to be a substrate for adenosine deaminase is more a function of the 2-substituent or lack thereof on the adenine portion of the molecule than a function of substituents on the linked sugar ring portion, at least as far as the substituents on both rings herein are concerned.

C. Methods

As noted earlier, a method of treating multiple sclerosis is contemplated herein. Broadly in that method, a patient having multiple sclerosis is treated with a composition containing a pharmacologically acceptable carrier having dissolved or dispersed therein, as an active ingredient, a substituted adenine derivative (substituted 2'-deoxyadenosine) whose structure corresponds to that of previously discussed Formula I. The substituted adenine derivative is present in the composition in an amount sufficient to provide a therapeutically effective dose over the period of contacting. The above treatment is typically repeated periodically such as weekly or monthly over a time period of several months to about one year.

The amount of a compound of Formula I present in a composition and used in a method as described above is a function of several variables. Among those variables is the method of administration. Exemplary concentrations for various modes of administration are illustrated hereinafter.

When the administration is in vivo, the amount administered is less than that which substantially impairs bone marrow functions as determined by usual procedures. An amount sufficient to kill at least about 50 percent of the monocytes originally present while not substantially impairing bone marrow function over the course of the administration of the agent is one way of defining a therapeutic dose.

The above amount of a 2'-deoxyadenine derivative of Formula I or its pharmacologically acceptable salt present in the composition is also an amount sufficient to provide about 0.04 to about 1.0 mg/kg of body weight of the treated host mammal per day, more preferably about 0.04 to about 0.20 mg/kg/day, more preferably still at about 0.05 to about 0.15 mg/kg/day and most preferably about 0.1 mg/kg/day, when given in vivo. This amount is another way of defining a therapeutically effective dose that is particularly useful when a compound of Formula I is administered by infusion.

The molar plasma concentration of the compound of Formula I or the pharmacologically acceptable salts thereof during treatment is preferably in the range of about 1 nanomolar (nM) to about 100 nM, particularly about 5 nM to about 50 nM, and more preferably about 10 nM to about 20 nM. Molarity of the 2'-deoxyadenine derivative in plasma of the treated (administered to) patient thus provides still another measure of a therapeutically effective dose from which the amount in a composition can be calculated.

It is to be understood that the above therapeutically effective dosages need not be the result of a single administration, and are usually the result of the administration of a plurality of unit doses. Those unit doses can in turn comprise portions of a daily or weekly dosage, and thus, the therapeutically effective dose is determined over the period of treatment (contacting).

Oral administration and subcutaneous injection are preferred modes of administration, as already noted. To achieve the desired plasma concentration of the agent, a range of doses can be employed depending upon the specific mode of administration, objective of the particular treatment, the particular compound being used, and like considerations.

For example, for oral administration, the daily dose can be about 0.04 to about 1.0 mg/kg of body weight, more preferably about 0.04 to about 0.20 mg/kg/day, more preferably still at about 0.05 to about 0.15 mg/kg/day, and most preferably about 0.1 mg/kg body weight. In general, the amount of active substituted adenine derivative administered can vary over a relatively wide range to achieve, and preferably maintain, the desired plasma concentration.

Unit dosage forms of the adenine derivative can contain about 0.1 milligrams to about 15 milligrams thereof. A preferred unit dosage form contains about 0.1 to about 1 milligram of agent and can be administered 2 to 5 times per day. However, it should be noted that continuous infusion at a rate designed to maintain the above described plasma concentration is also contemplated.

Duration of a particular treatment can also vary, depending on severity of the disease, whether the treatment is intended for an acute manifestation or for prophylactic purposes, and like considerations. Typical administration lasts for a time period of about 5 to about 14 days, with a 7-day time course being usual. Courses (cycles) of administration can also be repeated at monthly intervals, or parenteral unit dosages can be delivered at weekly intervals. Oral unit dosages can be administered at intervals of one to several days to provide the determined therapeutically effective dose. Thus, in vivo administration of a before-discussed dosage over a time period of about 5 to about 14 days or at weekly or daily intervals provides an amount sufficient to kill at least about 50 percent of the originally present monocytes.

This method of treatment produces a decrease in the level of monocytes in the blood due to the toxicity of the utilized compounds of Formula I toward monocytes. This method can be used to reduce the number of monocytes circulating in a treated mammal's blood stream by about 90 percent of the number present prior to treatment over a seven day treatment period with the level of circulating monocytes returning to pretreatment levels about two weeks after the treatment stopped. This exemplary study is illustrated hereinafter.

A less aggressive treatment regimen is also therefore contemplated. Here, a before-described dosage, e.g., plasma concentration, is again utilized, but for a shorter contact time course so that monocyte function is impaired, but the monocytes are not substantially killed as is the result of the before-discussed treatment regimen. Impairment of monocyte function is herein defined as a reduction of at least about 25 percent in the spontaneous secretion of interleukin-6 (IL-6) by monocytes cultured in the presence of a compound of Formula I for a time period of 72 hours. A useful assay for monocyte impairment is discussed hereinafter.

In an exemplary treatment regimen, a compound of Formula I is administered in an amount of about 0.04 to about 1.0 mg/kg/day, more preferably about 0.04 to 0.20 mg/kg/day, more preferably still about 0.05 to about 0.15 mg/kg/day, and most preferably about 0.1 mg/kg/day. Such treatments typically provide a plasma concentration of about 0.5 nM to about 50 μM, and more preferably about 10 nM to about 10 μM. That single administration is repeated periodically such as weekly over a time period of several months, e.g. about three to about nine months. In usual practice, treatments are administered over a period of about five to seven days and are repeated at about three to about four week intervals for several months, e.g. about three to about nine months.

Such an administration can be carried out on an outpatient basis for humans using an intravenous infusion lasting about 2 to about 4 hours in a doctor's office. As such, the treatment is far less invasive than is a continuous infusion over a period of several days that usually requires a hospital stay for the host mammal; i.e., human patient. A less invasive continuous infusion method that employs a pump linked to a catheter that automatically infuses a predetermined dosage permits the patient to be ambulatory during the infusion.

Any of the before-discussed methods can be carried out while the patient is continuing therapy with a previous drug or drugs, or after cessation of such prior treatment. When a patient is removed from a prior even partially effective treatment, a flareup (exacerbation) of symptoms sometimes occurs that typically abates after several months. In addition, where a prior treatment regimen is halted while an above method is practiced, that prior treatment can be continued after cessation of an above method, often with quite positive results.

Dosage schedules and protocols for administering 2-chlorodeoxyadenosine to treat patients having disease conditions other than multiple sclerosis have been reviewed in the literature. (Ernest Beutler (1992), The Lancet, 540: 952–956) To a first approximation, the pharmacokinetics of 2-chlorodeoxyadenosine and its effect upon monocyte levels are independent of the disease condition being treated.

D. Compound Synthesis

A compound useful herein where Z is absent can be prepared by condensing an appropriately substituted adenine directly with an appropriately substituted sugar ring as by the techniques described in Montgomery et al., (1986) J. Med. Chem., 29:2389– 2392, by the method taught in U.S. Pat. No. 4,082,911, or as described in the citations of Herdewijn et al. (1987) J. Med. Chem., 30:2131–2137, which disclosures are incorporated herein by reference. An appropriately substituted adenine can be prepared by following reported literature syntheses or analogous syntheses. Still further, Wright et al. (1987) J. Org. Chem., 35:4617–4618 recently prepared 2-chloro- and 2-bromo-2'-deoxyadenosines by direct reaction of the appropriate 2,6-dihalo purine with a 3',5'-protected-alpha-1-chlororibose using sodium hydride in acetonitrile, followed by treatment with methanolic ammonia at 60 degrees C. to deprotect the resulting 3',5'-hydroxyls and form the 6-amino group of the finally produced adenosine. Fukukawa et al. (1983) Chem. Pharm. Bull., 31(5):1582–1592 also report syntheses of 2'-deoxy- 2'-arahalo-substituted adenosine derivatives.

The 2,-deoxy-2'-fluoroarabinofuranosyladenine compounds of the present invention are produced as described hereinafter in the Examples. The synthesis is similar to that taught in Marquez et al. (1987) Biochem. Pharmacol., 36:2719–2722, herein incorporated by reference, in which 6-chloropurine is condensed with 3-O-acetyl-5-O-benzoyl-2-deoxy-2-fluoro-D-arabinofuranosyl bromide. The functionalized halosugar is produced according to the method reported by Reichman et al. (1975) J. Carbohyd. Res., 42:233 and the 2'-deoxy-2'-fluoroarabinofuranosyladenine compound is obtained by ammonolysis with concentrated methanolic ammonia which removes the protective groups. Syntheses of 2-substituted- 2'-deoxy-2'-arafluoroadenosines are also described in U.S. Pat. No. 4,918,179 and U.S. Pat. No. 5,034,518, whose disclosures are incorporated by reference.

The adenosine-1-N-oxide group of compounds, i.e, where Z is present, is of particular interest since those materials, per se, are most likely not incorporated into a growing polynucleotide chain because the presence of the N-oxide group probably interferes with hydrogen bonding during that synthesis. Rather, it is believed that the N-oxide compounds are reduced by an endogenous reductase prior to their incorporation into and termination of the growing chain.

Nevertheless, being free from a net ionic charge, but possessing an internal zwitterionic charge pair, the N-oxide compounds can penetrate cell membranes. Those compounds are also somewhat more water-soluble than are the corresponding un-oxidized compounds.

Without wishing to be bound by theory, it is nevertheless believed that the N-oxide compounds enter the cell and are phosphorylated, in keeping with the report of such phosphorylation in Lindberg et al. (1967) J. Biol. Chem., 242:350–356. A pool of such derivatives is maintained intracellularly until such time as the N-oxide function is reduced and the nucleotide is incorporated to terminate the appropriate, growing polynucleotide chain.

The 1-N-oxide compounds are readily prepared by the method of Klenow et al. (1961) Biochim. Biophys. Acta, 52:386-389, with slight modification, as discussed hereinafter.

The present invention is further illustrated by the following examples which are not intended to limit the scope of the invention in any way.

EXAMPLE 1

Treatment of Multiple Sclerosis with CdA

A study of four patients with chronic multiple sclerosis was undertaken. Each patient was first examined for normal hepatic, renal, and bone marrow functioning to establish baseline values. Each of the patients was then treated with CdA dissolved in sterile preservative-free isotonic saline. The CdA was administered intravenously at a dosage of 0.1 mg/kg each day for a total of seven days. Each patient received six courses of intravenous therapy, once monthly for a total of six months. Patients were examined on a daily basis while hospitalized. During that time, daily blood counts and twice weekly blood chemistries were performed on each patient. CdA levels were also measured in blood and spinal fluid.

The neurologic function of each of these patients was measured using the expanded Krutzke disability status scale (EDSS), and the Scripps neurologic rating scale (SNRS).

There was no evidence of any significant toxic side effects. None of the four patients exhibited any nausea, vomiting, skin rash, or hepatic or renal dysfunction. Each of the patients developed lymphopenia (reduction in the level of lymphocytes in the blood), with absolute lymphocyte counts being suppressed 0.5 to about 10 percent for more than one year.

Monocyte levels dropped after each treatment. For example, in one patient, monocytes dropped 40 percent after the first treatment, and were substantially absent after each of the remaining five treatments. For another patient, monocytes were substantially absent after two treatments, and depleted by about 85, 50, 40 and 73 percents after the other four treatments.

In some cases, there was leukopenia (reduction in the level of total white blood cells). There was also a modest macrocytosis in all patients lasting for six to eight months after cessation of treatment. However, the platelet counts of all four patients remained within the normal range. In essence, there was no evidence of toxicity in these four patients with normal marrow, hepatic and renal functions. Likewise, the side effects of CdA were imperceptible in these four patients.

Measurement of neurologic function using the EDSS and SNRS scales provided evidence of improvement in all four patients during treatment with CdA. Cerebrospinal fluid studies (CSF) showed a marked drop in lymphocyte counts and, quite remarkably, complete disappearance of IgG oligoclonal bonds in all cases. There was no significant change in total CFS IgG.

In particular, the SNRS data demonstrated between 5 and 50 percent improvement from baseline pretreatment values in all patients. One of the four patients was completely bed-ridden at the beginning of the treatment, and this patient was able to walk with the aid of a walker by the end of the treatment. All patients reported subjective feelings of improved energy and stamina.

EXAMPLE 2

Treatment of Multiple Sclerosis with CdA

The study indicated above in Example 1 involving four patients was then enlarged. A double-blind placebo study involving 50 patients was performed to further demonstrate the effectiveness of 2-CdA for treating multiple sclerosis. The dosage schedules and protocols for this second study were similar or substantially the same as the dosage schedules and protocols employed in Example 1. The same two neurologic rating scales were employed, i.e. the SNRS scale and the EDSS scale. 28 patients were tested with the SNRS scale; 23 patients were tested with the EDSS scale. The SNRS scale is substantially more sensitive than the EDSS scale. The inventor's most recent data indicate that a highly significant improvement (p=0.0004) was observed in patients treated with 2-CdA as compared with placebo in the 28 patients tested for changes in the SNRS scale.

TABLE I

|  | Absolute | Relative |  |
|---|---|---|---|
| Changes in SNRS | | | |
| CdA | 4.83 ± 5.71 | 0.076 ± 0.089 | (N = 14) |
| Placebo | −4.40 ± 5.14 | −0.062 ± 0.071 | (N = 14) |
|  | p = 0.0004 | p = 0.0005 |  |
| Changes in EDSS | | | |
| CdA | −0.018 ± 0.222 | −0.011 ± 0.081 | (N = 12) |
| Placebo | 0.038 ± 0.9233 | 0.039 ± 0.240 | (N = 11) |
|  | p = 0.84 | p = 0.50 |  |

| | | |
|---|---|---|
| SNRS | 0 | 100 |
| EDSS | 10 | 1 |
|  | Worst | Best |

The foregoing description and the examples are intended as illustrative and are not to be taken as limiting. Still other variations within the spirit and scope of this invention are possible and will readily present themselves to those skilled in the art.

What is claimed is:

1. A method of treating a patient having multiple sclerosis, the method comprising:

administering to said patient a composition containing a therapeutically effective dose of a substituted adenine derivative as an active ingredient dissolved or dispersed in a physiologically tolerable carrier to said patient, said substituted adenine derivative being administered in an amount sufficient to decrease the level of monocytes in the blood of said patient by at least about 50 percent during the course of said treatment and having a structure represented by the formula:

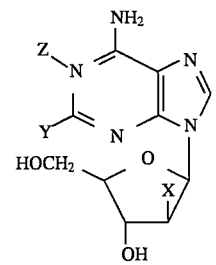

where Z is O⁻ or absent; Y is hydrogen or a substituent containing one to about 20 atoms that is free from net ionic charge at physiological pH values, produces a soluble adenine derivative, and whose presence on the adenine moiety inhibits deamination of said adenine derivative by adenosine deaminase; and X is hydrogen or fluoro, with the proviso that Y is hydrogen only when Z is present.

2. The method of claim 1 wherein said substituted adenine is administered in an amount of about 0.04 to about 0.20 milligrams per kilogram of body weight per day.

3. The method of claim 1 wherein said substituted adenine is 2-chloro-2'-deoxyadenosine.

4. The method of claim 1 where said administration is repeated periodically.

5. The method of claim 1 wherein said substituted adenine is administered to the patient by subcutaneous injection.

6. The method of claim 5 wherein said substituted adenine is 2-chloro-2'-deoxyadenosine.

* * * * *